United States Patent [19]

Schuppiser et al.

[11] Patent Number: 5,446,014
[45] Date of Patent: * Aug. 29, 1995

[54] CATIONIC COMPOUND/XANTHAN GUM AQUEOUS COMPOSITIONS

[75] Inventors: Jean-Luc Schuppiser, Claye Souilly; Magali Knipper, Paris, both of France

[73] Assignee: Rhone-Poulenc Chimie, Courbevoie, France

[*] Notice: The portion of the term of this patent subsequent to Mar. 12, 2008 has been disclaimed.

[21] Appl. No.: 737,901

[22] Filed: Jul. 26, 1991

Related U.S. Application Data

[63] Continuation of Ser. No. 373,182, Jun. 29, 1989, abandoned, which is a continuation of Ser. No. 158,721, Feb. 23, 1988, abandoned.

[30] Foreign Application Priority Data

Feb. 23, 1987 [FR] France ................... 87 02294

[51] Int. Cl.$^6$ ............... A01N 43/40; A01N 33/12; A01N 25/00
[52] U.S. Cl. ................... 504/250; 504/234; 504/345; 71/DIG. 1; 514/334; 514/642; 514/643; 514/777; 435/104
[58] Field of Search ............ 71/94, DIG. 1, 121; 514/316, 642, 643, 406, 334, 777; 504/345, 250, 280, 281, 282, 234

[56] References Cited

U.S. PATENT DOCUMENTS

| | | | |
|---|---|---|---|
| 3,717,452 | 2/1973 | Gibsen et al. | 504/323 |
| 3,899,437 | 8/1975 | Regan et al. | 252/106 |
| 3,920,443 | 11/1975 | Drewe et al. | 504/245 |
| 4,764,206 | 8/1988 | Yamashita et al. | 504/250 |
| 4,874,423 | 10/1989 | Colegrove et al. | 504/250 |
| 4,999,047 | 3/1991 | Schuppiser | 504/234 |

FOREIGN PATENT DOCUMENTS 0032293 7/1981 European Pat. Off. .
2235959 2/1973 Germany .

*Primary Examiner*—Allen J. Robinson
*Assistant Examiner*—John D. Pak
*Attorney, Agent, or Firm*—Burns, Doane, Swecker & Mathis

[57] ABSTRACT

Precipitate-free aqueous compositions, well adapted as agricultural chemicals, e.g., crop protectants, are comprised of at least one water soluble cationic organic compound, e.g., a pesticidally active quaternary ammonium compound, and a thickening amount of a xanthan gum having an intrinsic viscosity of less than 3,500 cm$^3$/g.

2 Claims, No Drawings

CATIONIC COMPOUND/XANTHAN GUM AQUEOUS COMPOSITIONS

This application is a continuation, of application Ser. No. 07/373,182, filed Jun. 29, 1989, now abandoned, which is a continuation of application Ser. No. 07/158,721, filed Feb. 23, 1988 (now abandoned).

BACKGROUND OF THE INVENTION

1. Field of the Invention

The present invention relates to novel compositions of matter comprising aqueous formulations of a cationic organic compound and a xanthan gum, and, more especially, to aqueous plant protection compositions comprising a cationic active agent.

2. Description of the Prior Art

Xanthan gum, because of its thickening properties, its high suspending ability and its particular rheology, is widely used in various industries, particularly in the food, construction, textile, paint, paper, and cosmetic industries, and also in the agriculture and petroleum industries, etc.

Xanthan gum is an anionic heteropolysaccharide which consists of D-glucose, D-mannose and D-glucuronic acid units, with acetyl and pyruvate radicals bonded to the mannose units. Its molecular weight is greater than $10^6$. As it is advantageous in the aforesaid different applications to have a relatively low concentration of the thickening agent, the industrial grades currently available commercially have high viscosities, corresponding to molecular weights ranging from $3 \times 10^6$ to $5 \times 10^6$.

In view of its anionic character, xanthan gum is considered to be generally incompatible with cations, thus militating against its formulation therewith. Moreover, it is known in the agricultural chemicals field to use xanthan gum as an agent to thicken aqueous compositions containing a water soluble active pesticidal agent, or as a stabilizing and suspension agent for flowable aqueous dispersions containing a finely divided active agent ("flowables"). These solutions or dispersions are supplied commercially in the form of a concentrate with 20% to 60% active material and approximately 0.02 to 2% xanthan gum. However, if the active agent is water soluble, this application is limited, in actual practice, to nonionic or anionic materials.

A user, who in certain cases wishes (in order to avoid several manipulations) to mix the dilute dispersion of a water insoluble pesticide in water with a water soluble pesticide, such as a quaternary ammonium salt, is thus confronted with a particular problem. It has been found that with low xanthan concentrations in dilute formulations, a complex is formed with the quaternary ammonium compound, which results in the formation of dense fibers that are insoluble in water. In addition to the fact that the formation of the complex reduces the pesticidal activity, considerable difficulties are encountered during spraying in the field because of the clogging of the spray nozzles by the insoluble fibers.

SUMMARY OF THE INVENTION

Accordingly, a major object of the present invention is the provision of improved pseudoplastic aqueous compositions thickened by a xanthan gum and containing a cationic additive, which improved compositions may be diluted without precipitation.

Briefly, the present invention features concentrated, flowable pesticidal compositions of matter containing both a finely divided active agent that is insoluble in water, as well as a water soluble cationic active agent, in a manner such that the water soluble material is not precipitated by dilution to form objectionable precipitates during field applications.

DETAILED DESCRIPTION OF THE PREFERRED EMBODIMENTS OF THE INVENTION

More particularly according to the present invention, provided hereby are concentrated, flowable dispersions containing a finely divided active pesticidal agent that is insoluble in water, which dispersions can be diluted with water and a water soluble cationic active agent may be added thereto without concomitant precipitation.

While not wishing to be bound by any particular theory, it has thus been determined that there exists a correlation between the ability of xanthan gum to form complexes with cationic agents and the intrinsic viscosity of xanthan gum.

According to the present invention, the aqueous compositions of matter are characterized in that they contain at least one water soluble, cationic organic compound and a xanthan gum having an intrinsic viscosity less than 3,500 cm$^3$/g, measured in an aqueous NaCl solution (0.1M—distilled water) at 23° C., by means of a LOW-SHEAR ® apparatus.

The preparation of xanthan gum by the fermentation of a carbohydrate under the action of an appropriate microorganism has been described in numerous publications. Compare, for example, U.S. Pat. Nos. 3,020,206, 3,020,207 and 3,391,060. Exemplary of such microorganisms, generally representative are bacteria of the genus Xanthomonas, and more particularly *Xanthomonas campestris*, as well as the other microorganisms that are reported in the literature to produce heteropolysaccharides of a similar nature.

The xanthan gum incorporated into the compositions of the invention, and having an intrinsic viscosity less than 3,500 cm$^3$/g, may be obtained by varying the conditions of fermentation (see, for example, EP-A-32,293) or by treating a high viscosity gum. The degradation into a material having a lower viscosity may be effected by the action of heat, an enzyme, an oxidizing agent, a radical-like agent, or by acid hydrolysis, either directly on the fermentation wort prior to the precipitation of the gum, or on a solution reconstructed from powder.

The intrinsic viscosity $[\eta]$ as specified above, is determined by the extrapolation to zero concentration of the reduced viscosity $(\eta - \eta_o)/\eta_o c$ (wherein $\eta$ is the viscosity of the solution, $\eta_o$ is the viscosity of the solvent and c is the concentration of xanthan gum) using the Huggins equation:

$$(\eta - \eta_o)/\eta_o c = [\eta] + k' [\eta]^2 c$$

The specific viscosity $(\eta - \eta_o)/\eta_o$ is measured on aqueous solutions with 0.1M NaCl as the solvent, in a xanthan concentration between 0 and 0.04% by weight/volume. The measurements are carried out at 23° C. with a shear between 0 and 1 sec$^{-1}$ using the LOW-SHEAR ® apparatus marketed by the Contraves Co. The curve of specific viscosity is plotted as a function of concentration and is extrapolated to zero concentration.

The water soluble cationic compositions which form insoluble complexes with the xanthan gum are principally the quaternary ammonium hydroxides and salts, such as chlorides, bromides, sulfates, bromates, acetates, formates, citrates, lactates, maleates, proprionates, phosphates, succinates, tartrates, toluene sulfonates. Representative examples of quaternary ammonium compounds which react with heteropolysaccharides are described in U.S. Pat. No. 3,163,602, hereby incorporated by reference. Quaternary ammonium compounds which include an alkyl moiety are hydrophobic in character and difunctional quaternary ammonium compounds are particularly able to form insoluble complexes.

Cationic compounds and particularly quaternary ammonium compounds, are used in various applications, for example in the textile, paint, agricultural and detergent industries. They are capable of serving, notably, as surface active agents, antiseptic agents, germicides, colorants, softeners, and the like. Representative examples of such compounds currently in use include, without limitation, the n-alkyldimethylbenzylammonium and n-dialkylpyridynium chlorides and bromides, in which the alkyl chain preferably contains 8 to 24 carbon atoms, such as dodecyltrimethylammonium chloride, hexadecyltrimethylammonium bromide, lauryldimethylammonium bromide, didecyldimethylbenzylammonium chloride, hexadecylpyridinium chloride, etc.

In the phytosanitary field, quaternary ammonium compounds are used as active ingredients having pesticidal activity, such as bactericides, insecticides, fungicides, herbicides, algacides, acaricides, nematicides, plant growth regulators. As specific examples of commercial products, the following are representative: 1,1'-dimethyl-4,4'-bipyridinium 1-dichloride or paraquat; 1,1'-dimethyl-4,4'-bipyridinium dimethylsulfate, 1,1'-ethylene-2,2'-bipyridinium dibromide or diquat; 1,2-dimethyl-3,5-diphenylpyrazolium methylsulfate or difenzoquat; 2-chloroethyltrimethylammonium chloride or chlormequat; 1-allyl-1-(3,7-dimethyloctyl) piperidinium bromide or piproctanyl; 1,1'-bis-3,5-dimethylmorpholinocarbonylmethyl-4,4,-bipyridinium dichloride or morfamquat. Other useful compounds include 1,1'-di-2-hydroxyethyl-4,4'-bipyridinium dichloride, 1-(2-hydroxyethyl)-1'-methyl-4,4'-bipyridinium dichloride, 1,1'-dicarbamoyl-4,4'-bipyridinium dichloride, 1,1'-bis-N,N-dimethylcarbamoylmethyl-4,4'-bipyridinium dichloride, 1,1'-bis-N,N-diethylcarbamoylmethyl-4,4'-bipyridinium dichloride, 1,1'-di-bis-N,N-diethylcarbamoylmethyl-4,4'-bipyridinium dichloride, 1,1'-di-(piperidinocarbonylmethyl)-4,4'-bipyridinium dichloride, 1,1'-diacetonyl-4,4'-bipyridinium dichloride, 1,1'-diethoxycarbonylmethyl-4,4'-bipyridinium dibromide, and 1,1'-diallyl-4,4'-bipyridinium dibromide.

The xanthan gum and the cationic compound are present in the subject compositions in amounts that are usual for the end applications under consideration. The invention does not require any particular dosage, as its principal object is the stabilization of the xanthan gum, which is a minor component of the compositions.

In pourable and pumpable compositions, the xanthan is generally present in amounts ranging from 0.005 to 2%. Advantageously, the dilute compositions contain the xanthan gum in amounts less than 0.1%. The amount of the cationic compound may vary greatly, for example, from 0,001% to 2.5% in dilute solutions and from 0.5% to 70% in concentrates.

The compositions according to the invention may also contain the usual additives, such as surface active agents, antifoaming agents, agents for lowering freezing point, fillers, and the like.

The compositions of the invention may be prepared by simple admixing of the ingredients under agitation, at ambient temperature. They may be present in the form of a concentrated or dilute solution or suspension containing at least one cationic organic compound and the xanthan gum in solution in water. It is preferable to initially dissolve the xanthan gum in water and then add the water soluble cationic compound, and, optionally, the other ingredients, and then dilute the solution to the required concentration at the site of the particular end application.

The compositions may be diluted with water in any proportion to provide solutions free of agglomerates or fibrous precipitates associated with the formation of complexes between the xanthan gum and the cationic compound.

The pesticidal compositions of the invention contain, in addition, a finely divided pesticidally active substance insoluble in water, which may be added simultaneously with the conventional additives. In the dilute form, which may be applied by spraying, these compositions may also be prepared by dilution of an aqueous concentrate containing an insoluble active substance having pesticidal activity, in suspension in a liquid thickened by xanthan gum, and by the solubilization to the extent required of the water soluble cationic active substance having pesticidal activity. The dilute compositions prepared from a composition according to the invention may be applied by means of any type of spraying equipment without clogging the spray nozzles.

In order to further illustrate the present invention and the advantages thereof, the following specific examples are given, it being understood that same are intended only as illustrative and in nowise limitative. In particular, the compatibility of the dilute aqueous solutions of xanthan gum having a relatively low intrinsic viscosity with a cationic quaternary ammonium compound is illustrated in said examples to follow.

EXAMPLE 1

A xanthan gum wort prepared under standard conditions for industrial applications was degraded by heat treatment such as to provide different lots having variable intrinsic viscosities $[\eta]$. In each lot the xanthan gum was precipitated by isopropanol, dried and ground. The intrinsic viscosities were determined in the above-indicated manner the xanthan gum precipitated from the initial wort without degradation had a $[\eta]$ of 4,500 cm$^3$/g.

From each lot, aqueous solutions with concentrations of 0.1%, 0.05% and 0.005% were prepared. To each of the solutions, under agitation, a 10% aqueous solution of 1,1'-dimethyl-4,4'-bipyridinium dichloride (Paraquat), marketed by I.C.I., was added, such as to provide an active ingredient concentration of from 0.01 to 0.2%. The precipitation of the complex of the xanthan gum and the quaternary ammonium compound, if indeed it occurred, was immediate, in the form of insoluble fibers.

The different experiments, observations and results are reported in Table I. The xanthan gum was considered to be incompatible, if long fibers having dimensions larger than approximately 2 mm and a coarse texture, were formed.

It was found that:

(i) for xanthan concentrations of 0.1%, the gum was compatible with Paraquat, regardless of the value of $[\eta]$;

(ii) compatibility declined as a function of the xanthan concentration;

(iii) the formation of the complex in the form of long fibers decreased with declining values of $[\eta]$. For a value less than 3,500 cm³/g, the xanthan gum was considered to be compatible in all useful proportions with Paraquat.

TABLE I

| xanthan gum % | $[\eta]$ cm³/g | Paraquat % | | | | |
|---|---|---|---|---|---|---|
| | | 0.01 | 0.02 | 0.05 | 0.1 | 0.2 |
| 0.005 | 2000 | 0 | 0 | 0 | 0 | 0 |
| | 2700 | 0 | 0 | 0 | 0+ | 0+ |
| | 3500 | 0 | 0+ | + | + | + |
| | 4500 | + | + | + | + | + |
| 0.05 | 2000 | 0 | 0 | 0 | 0 | 0 |
| | 2700 | 0 | 0 | 0 | 0 | 0 |
| | 3500 | 0 | 0 | 0 | 0+ | 0+ |
| | 4500 | 0+ | + | + | + | + |
| 0.1 | 2700 | 0 | 0 | 0 | 0 | 0 |
| | 4500 | 0 | 0 | 0 | 0 | 0 |

0: absence of fibers
0+: rare fibers 1 to 2 mm long - fine texture - COMPATIBLE
+: fibers longer than 2 mm - coarse texture - INCOMPATIBLE

EXAMPLE 2

Using the xanthan gum lots prepared by the procedure of Example 1, 0.01% by weight aqueous solutions were prepared. In each of the solutions, a quantity of lauryl dimethyl benzylammonium bromide (CEQUARTYL A ®) was dissolved, such as to provide a surface active concentration of from 0.01% to 1%. The results relative to the precipitation of the complex are reported in Table II:

TABLE II

| xanthan gum % | $[\eta]$ cm³/g | Cequartyl A % | | | | |
|---|---|---|---|---|---|---|
| | | 0.01 | 0.02 | 0.05 | 0.1 | 1 |
| 0.01 | 2000 | 0 | 0 | 0 | 0 | 0 |
| | 2700 | 0 | 0 | 0 | 0 | 0 |
| | 3500 | 0+ | + | + | + | + |
| | 4500 | + | + | + | + | + |

0: absence of fibers
0+: rare fibers of 1 to 2 mm - fine texture
+: fibers longer than 2 mm - coarse texture - INCOMPATIBLE

EXAMPLE 3

Aqueous solutions with 0.01% to 0.005% xanthan gum and variable $[\eta]$ were prepared. In each of the solutions, a quantity of didecyldimethylbenzylammonium chloride (bactericide) was dissolved, such that the concentration of the active ingredient ranged from 0.002% to 0.006% by weight. The results obtained are reported in Table III.

TABLE III

| xanthan gum % | $[\eta]$ cm³/g | Didecyldimethylbenzylammonium chloride | | | |
|---|---|---|---|---|---|
| | | 0.002 | 0.003 | 0.004 | 0.006 |
| 0.005 | 3000 | 0 | 0 | 0 | 0 |
| | 3200 | 0 | 0 | 0+ | + |
| | 5100 | + | + | + | + |
| 0.01 | 3000 | 0 | 0 | 0 | 0 |
| | 3200 | 0 | 0 | + | + |
| | 5100 | + | + | + | + |

0: absence of fibers
0+: rare fibers of 1 to 2 mm - fine texture
+: long fibers - coarse texture - INCOMPATIBLE

EXAMPLE 4

A concentrated liquid suspension of atrazine [2-chloro-4-ethylamino-6-isopropylamino(1,3,5-triazine)] was prepared:

| (i) | Atrazine | 400 g/l |
|---|---|---|
| (ii) | Anionic surfactant | 30 g/l |
| (iii) | Xanthan gum $[\eta]$ 2,700 cm³/g | 1.6 g/l |
| (iv) | Water q.s.p. | 1 liter |

40 ml of the concentrated liquid suspension were diluted in 940 ml of distilled water, 20 ml Paraquat in a 2% aqueous solution were added. No formation of insoluble fibers was observed.

By comparison, an identical formulation, but prepared using xanthan gum of $[\eta]$ 4,500 cm³/g, formed dense fibers immediately after addition of the Paraquat under the same conditions of dilution.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A precipitate-free solution, in water, consisting essentially of water, 0.01 to 0.2% by weight of paraquat and 0.005 to 0.05% by weight of a xanthan gum which has an intrinsic viscosity of less than 3,500 cm³/g, measured in a distilled water 0.1M NaCl solution at 23° C.

2. A precipitate-free solution, in water, consisting essentially of water, 0.01 to 0.2% by weight of paraquat, 0.005 to 0.05% by weight of a xanthan gum which has an intrinsic viscosity of less than 3,500 cm³/g, measured in a distilled water 0.1M NaCl solution at 23° C., and one or more additives selected from the group consisting of surface active agents, antifoaming agents, and agents for lowering freezing point.

* * * * *